(12) United States Patent
Demers et al.

(10) Patent No.: US 8,345,094 B2
(45) Date of Patent: Jan. 1, 2013

(54) SYSTEM AND METHOD FOR INSPECTING THE INTERIOR SURFACE OF A PIPELINE

(75) Inventors: Daniel Demers, Rigaud (CA); Ludovic Legendre, Montreal (CA); Frederic Otis, Laval (CA)

(73) Assignee: Quebec Inc. (C-Tec), Laval, Quebec ( * ) Notice: Subject to any disclaimer, the term of this patent is extended or adjusted under 35 U.S.C. 154(b) by 536 days.

(21) Appl. No.: 12/515,633

(22) PCT Filed: Nov. 20, 2007

(86) PCT No.: PCT/CA2007/002108
§ 371 (c)(1),
(2), (4) Date: Dec. 23, 2009

(87) PCT Pub. No.: WO2008/061365
PCT Pub. Date: May 29, 2008

(65) Prior Publication Data
US 2010/0157043 A1 Jun. 24, 2010

(30) Foreign Application Priority Data
Nov. 20, 2006 (CA) .................................... 2568021

(51) Int. Cl.
*H04N 7/18* (2006.01)

(52) U.S. Cl. .......................... 348/84; 73/1.01; 348/125

(58) Field of Classification Search .................. None
See application file for complete search history.

(56) References Cited

U.S. PATENT DOCUMENTS

| | | | | |
|---|---|---|---|---|
| 4,607,925 A | * | 8/1986 | Kamigaichi et al. | 396/19 |
| 4,855,838 A | * | 8/1989 | Jones et al. | 348/84 |
| 4,963,984 A | * | 10/1990 | Womack | 348/176 |
| 5,059,019 A | * | 10/1991 | McCullough | 352/131 |

(Continued)

FOREIGN PATENT DOCUMENTS

DE 20308761 U1 11/2004

(Continued)

OTHER PUBLICATIONS

International Search Report of Application No. PCT/CA2007/002108 dated Jan. 25, 2008.

*Primary Examiner* — Moustafa M Meky
*Assistant Examiner* — Clayton R Williams
(74) *Attorney, Agent, or Firm* — Pearl Cohen Zedek Latzer, LLP

(57) ABSTRACT

An inspection system for inspecting an interior surface of a pipeline has a frame adapted to travel in the pipeline and an imaging means for imaging a selected portion of the interior surface of the pipeline. The imaging means has a field of view and is mounted in a rotatable manner on the frame. The inspection system has with a two-dimensional pattern generator for generating a two-dimensional pattern projection. The generator is mounted with the imaging means to project the two-dimensional pattern projection in the field of view thereof. The imaging means provide images of the selected portion of the internal surface comprising the two-dimensional pattern projection for monitoring a perpendicularity of the optical axis of the imaging means with respect to the selected portion of the interior surface of the pipeline thanks to a shape of the two-dimensional pattern projection prior to inspection of the internal surface.

13 Claims, 5 Drawing Sheets

U.S. PATENT DOCUMENTS

| | | | |
|---|---|---|---|
| 5,362,962 A * | 11/1994 | Barborak et al. | 250/234 |
| 5,513,276 A * | 4/1996 | Theodoracatos | 382/154 |
| 6,043,891 A | 3/2000 | Hartrumpf et al. | |
| 6,057,967 A * | 5/2000 | Takahashi et al. | 359/641 |
| 6,931,149 B2 * | 8/2005 | Hagene et al. | 382/141 |
| 2002/0011367 A1 * | 1/2002 | Kolesnik | 180/168 |
| 2003/0016285 A1 | 1/2003 | Drost et al. | |
| 2005/0104600 A1 * | 5/2005 | Cotton | 324/519 |
| 2006/0152589 A1 * | 7/2006 | Morrison et al. | 348/208.1 |

FOREIGN PATENT DOCUMENTS

EP          474293          3/1992

\* cited by examiner

SYSTEM AND METHOD FOR INSPECTING THE INTERIOR SURFACE OF A PIPELINE

FIELD OF THE INVENTION

The present invention generally relates to the field of visual inspection, and more particularly concerns an inspection system for inspecting the interior surface of a pipeline that provides improved measurements of defects such as the measure of the width of a crack. The invention also provides an inspection method.

BACKGROUND OF THE INVENTION

The presence of longitudinal fissures in concrete pipes is a main concern when the time comes to determine the condition of the pipes. According to the standards of the industry, the width of the crack has to be correctly determined in order to classify the defect.

In the art, several tools particularly adapted to provide images of the internal surface of a pipe have been proposed and are currently used. These tools are generally provided with a vehicle adapted to travel in the pipe and an imaging means such as a camera mounted on the vehicle. The vehicle is generally operatively connected to a control unit mounted in the inspection truck proximate the pipe under inspection. An operator inside the truck controls manually the traveling of the vehicle as well as the orientation of the camera to visually inspect the internal surface of the pipe. The grabbed images are generally recorded as a video sequence and the operator can index and comment particularly pertinent images for further review.

The analyst in charge of the observation of the points of interest such as supposed defects, either directly in the truck during the recording of the images or either subsequently to the recording in a central processing center for example, then determines subjectively the severity of the defect.

These inspection systems are well adapted for a coarse visual inspection but can not provide an accurate measure of a defect such as the precise width of the crack at particular point. The visual inspection of the condition of the internal surface of the pipe then depends on the judgment of the operator in charge without relying on an accurate and reliable measure.

Known in the art, there is US patent application published under no. 2003/0016285 which describes an imaging apparatus and method devised to provide accurate measurement of the defects. The described system is however quite complex to implement and not enough heavy-duty, especially for a specific use in small underground sewage pipes.

Other inspection systems using ultrasonic or magnetic devices have also been proposed. These systems do not however provide accurate and reliable measures of the defects.

Therefore, there is a need for an improved system for inspecting the interior surface of a pipeline that would provide accurate and reliable measures of the defects.

The pipelines that generally require a visual inspection for checking their integrity are often underground pipelines. Moreover, these pipes can be of a quite small diameter, as small as eight inches for example. It would therefore be even more desirable to provide an inspection system particularly adapted for inspection of pipes of reduced diameter.

SUMMARY OF THE INVENTION

An object of the present invention is to provide an inspection system that satisfies the above mentioned needs.

Accordingly, the present invention provides an inspection system for inspecting an interior surface of a pipeline. The system has a frame adapted to travel in the pipeline and an imaging means for imaging a selected portion of the interior surface of the pipeline. The imaging means has an optical axis and a field of view and is mounted in a rotatable manner on the frame. The inspection system is also provided with a two-dimensional pattern generator for generating a two-dimensional pattern projection. The generator is mounted with the imaging means to project the two-dimensional pattern projection in the field of view of the imaging means. The imaging means provide images of the selected portion of the internal surface comprising the two-dimensional pattern projection for monitoring a perpendicularity of the optical axis of the imaging means with respect to the selected portion of the interior surface of the pipeline thanks to a shape of the two-dimensional pattern projection prior to inspection of the internal surface.

Advantageously, the inspection system of the present invention provides accurate and reliable measures of the defects, and more particularly of the width of a longitudinal crack, thereby allowing to classify the localised defect according to industry standards.

In a preferred embodiment, the inspection system has a processing unit for processing at least one of the images to determine the width of a longitudinal crack. The processing unit is further adapted to calibrate the inspection system responsively to the shape of the two-dimensional pattern projection for still providing accurate measures even if the optical axis of the imaging means does not extend perpendicularly to the selected portion of the interior surface under inspection.

According to another aspect of the invention, there is also provided a method for inspecting an interior surface of a pipeline. The method comprising steps of:
a) providing an inspection system adapted to travel in the pipeline, the inspection system being provided with imaging means for imaging a selected portion of the interior surface of the pipeline;
b) projecting a two-dimensional pattern projection on the selected portion of the interior surface of the pipeline in the field of view of the imaging means;
c) imaging the selected portion comprising the two-dimensional pattern projection; and
d) monitoring a shape of the two-dimensional pattern projection for monitoring a perpendicularity of the optical axis of the imaging means with respect to the selected portion of the interior surface of the pipeline prior to inspection thereof.

Preferably, the method also comprises the steps of calibrating the inspection system according to the shape of the two-dimensional pattern projection and measuring a physical characteristic of the selected portion of the internal surface according to the perpendicularity of the optical axis of the imaging means.

BRIEF DESCRIPTION OF THE FIGURES

These and other objects and advantages of the invention will become apparent upon reading the detailed description and upon referring to the drawings in which.

Figure 1:
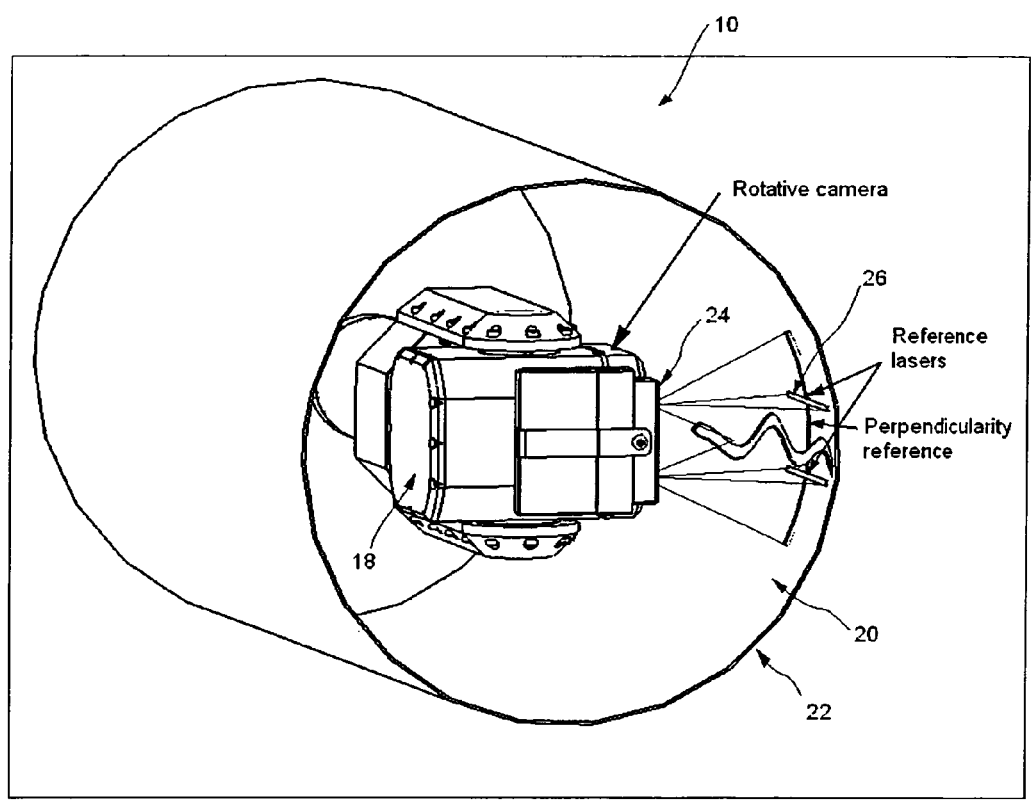
FIG. 1 is a perspective partial view of an inspection system shown in a pipeline, according to the present invention.

While the invention will be described in conjunction with example embodiments, it will be understood that it is not intended to limit the scope of the invention to such embodiments. On the contrary, it is intended to cover all alternatives, modifications and equivalents as may be included as defined by the present description and the appended claims.

DETAILED DESCRIPTION OF PREFERRED EMBODIMENTS OF THE INVENTION

In the following description, similar features in the drawings have been given similar reference numerals and in order to weight down the figures, some elements are not referred to in some figures if they were already identified in a precedent figure.

The present invention is directed to an inspection system for inspecting the interior surface of a pipeline providing accurate and reliable measures of the detected defects, and more particularly of the width of longitudinal cracks, thereby allowing to classify the localised defects according to industry standards. In a preferred embodiment that will be described below, a precision of the order of the hundredth of millimeter can be obtained.

The system of the present invention is particularly advantageous over the known prior art device using a camera for imaging the surface under inspection in that it allows to determine the perpendicularity of the optical axis of the camera with respect to the inspected surface prior to perform calculation on the images. Once the perpendicularity of the optical axis of the camera has been determined, an operator can rotate the camera in the convenient orientation to obtain images that would allow to precisely calculate the width of the crack. Indeed, it is known that a non perpendicularity will introduce imprecision in the image based calculations. Of course, as it will be more detailed thereinafter, the camera could be automatically controlled. In an alternate embodiment, the image based calculations can be made on images obtained with a non perpendicular angle, the calculation unit being adapted to correct the calculations according to the non perpendicular angle while still providing accurate measures.

The inspection system of the present invention is mainly devised to be used inside underground concrete pipes such as sewage pipes for example of a diameter varying between 8 and 36 inches for detecting and measuring the width of longitudinal cracks, but it should be mentioned that the present system could also advantageously be used in any tubular structure such as duct conducts.

It is also worth mentioning that although the present invention is particularly useful for measuring the width of a longitudinal crack, it can also be used for measuring its length, as well as any physical characteristic of the internal surface.

Figure 2:
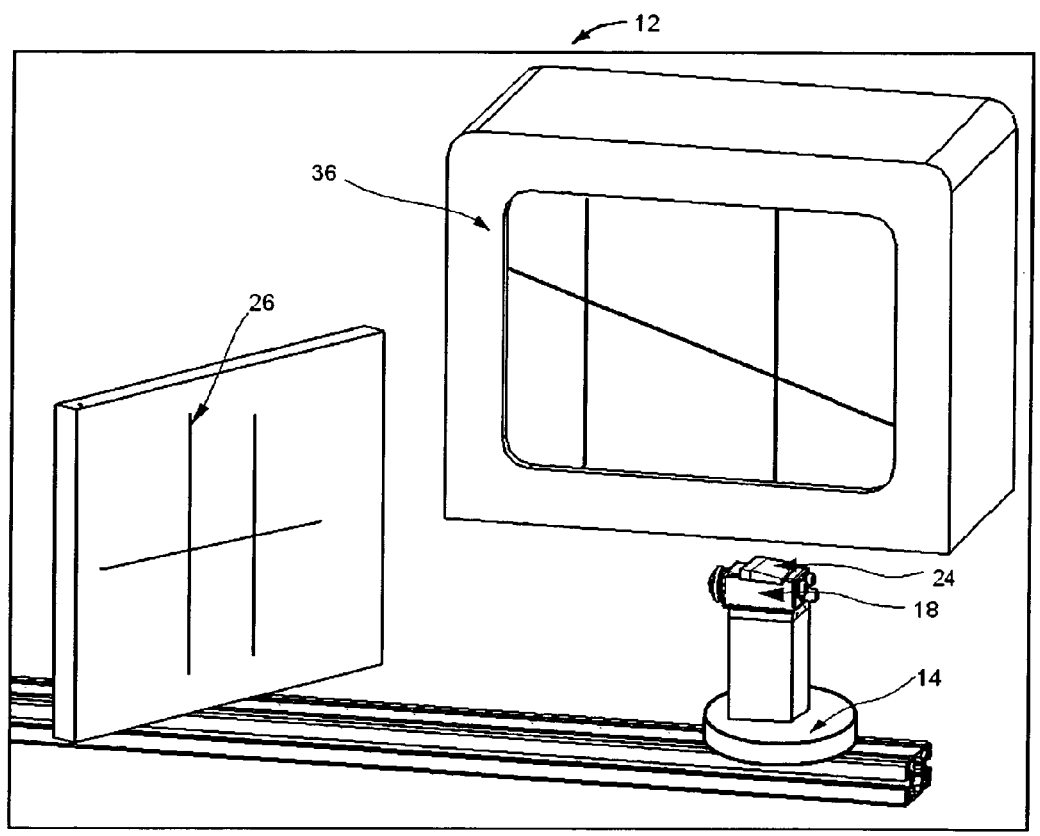
FIG. 2 is a perspective view of a setup of the inspection system according to the principles of the present invention.

Reference is now made to FIGS. 1 and 2 which respectively show an inspection system 10 and an experimental setup 12 according to the principles of the present invention. The inspection system 10 has a frame 14 adapted to travel in the pipeline 22 and an imaging means, preferably a camera 18, for imaging a selected portion of the internal surface 20 of the pipeline 22. The imaging means has an optical axis and a field of view, and is mounted in a rotatable manner on the frame 14 so as to allow to image each portion of the internal surface 20 of the pipeline 22. Preferably, the inspection system 10 has a light source (not shown) for lighting the selected portion of the internal surface 20 of the pipeline 22 and providing images of enhanced quality. The inspection system 10 is also provided with a two-dimensional pattern generator 24 for generating a two-dimensional pattern projection 26. The generator 24 is mounted with the camera 18 to project the two-dimensional pattern projection 26 in the field of view of the camera 18. Thus, the camera 18 is capable of providing images of the selected portion of the internal surface 20 comprising the two-dimensional pattern projection 26 for monitoring a perpendicularity of the optical axis of the camera 18 with respect to the selected portion of the internal surface 20 of the pipeline 22 thanks to a shape of the two-dimensional pattern projection 26 prior to inspection of the internal surface 20. Indeed, in the preferred case wherein the generator 24 is preferably fixed with respect to the camera 18, the shape of the projection 26, i.e. its deformation, on the surface 20 under inspection provides indications on the orientation of the camera 18 with respect to the surface 20 under inspection. It could also be considered that the generator 24 be movably mounted with respect to the camera 18. In this case, means for monitoring the angular and/or spatial relative position of the generator 24 should advantageously be provided.

In a preferred embodiment, the generator 24 is advantageously mounted proximate the optical axis of the camera 18 to project the two-dimensional pattern projection 26 in parallel with the optical axis of the camera 18. This would improve the precision of the measures. Of course, the generator 24 can also be mounted angularly with respect to the optical axis of the camera 18 without departing from the scope of the present invention. In fact, a person well versed in the art of the present invention will understand that any known two-dimensional projection 26 whose parameters are well known can provide in the images indications on the orientation of the camera 18 with respect to the surface 20 as well as on the distance between the surface 20 and the camera 18 possibly. Indeed, for a specific pattern projection, specific dimensions of the projection are known. From the distance in pixels in the image of these specific dimensions and with the rule of three, the dimension of a specific characteristic in the image could be easily obtained.

Figure 3A:
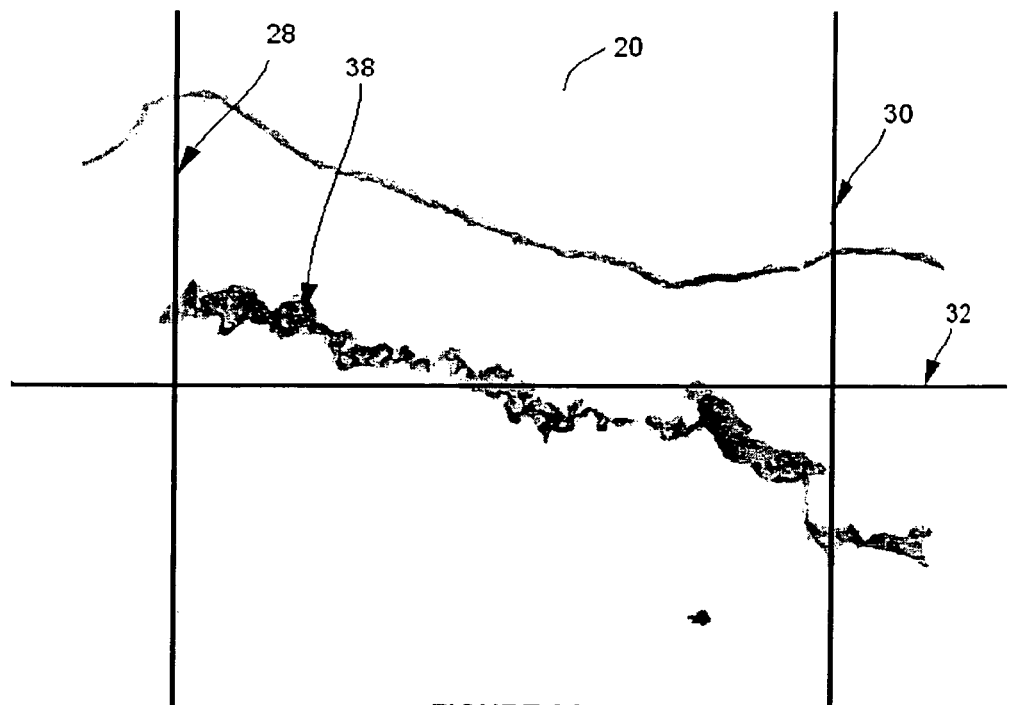
FIG. 3A shows an image of a longitudinal crack obtained with the system of the present invention.
Figure 3B:
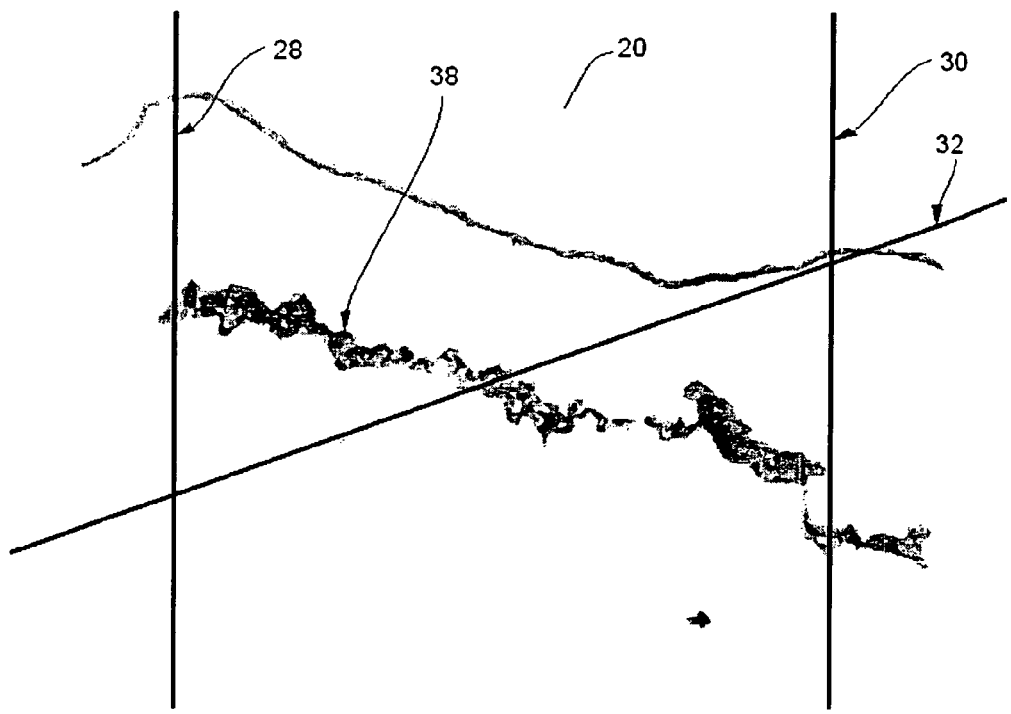
FIG. 3B shows another image of a longitudinal crack obtained with the system of the present invention.
Figure 5:
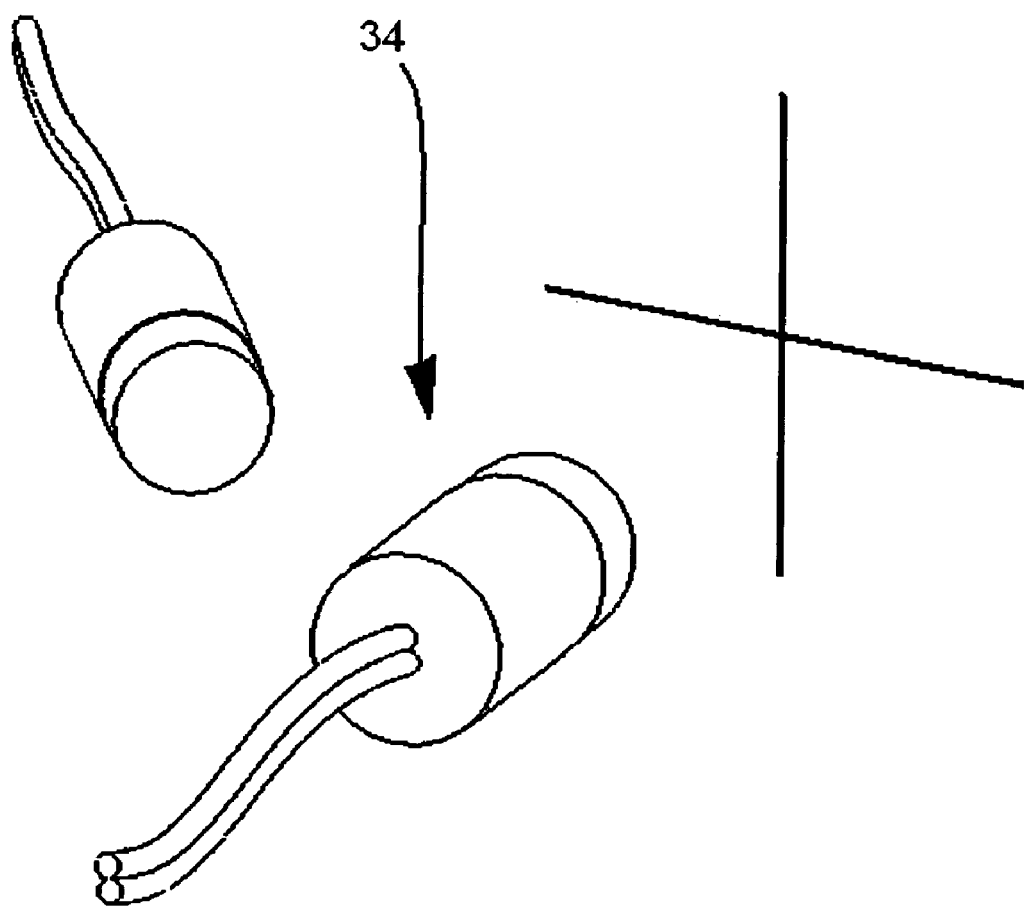
FIG. 5 shows two laser projectors for projecting a laser cross.

FIGS. 3A and 3B illustrates the projection 26 of a predetermined two-dimensional pattern on the surface 20 under inspection, in the preferred case wherein the generator 24 is mounted proximate the optical axis of the camera 18 and projects the pattern projection 26 in parallel thereto. The pattern projection 26 has a first and a second line projection 28, 30 parallel to each other and a third line projection 32 perpendicular to the first and second and is H-shaped, although other shapes such as a U or a N shape could be considered. In FIG. 3A, the optical axis of the camera 18 extends perpendicularly to the surface 20 under inspection while, in FIG. 3B, the optical axis of the camera 18 is at an angle with respect to the perpendicular. The deformation of the projection 26 proving the non perpendicularity of the camera 18 with respect to the surface 20 is clearly shown. In the illustrated case, a first and a second laser generator 34 as those shown in FIG. 5 for respectively generating a first and a second laser cross are advantageously used to generate the H-shape.

As previously mentioned, the two-dimensional pattern projection 26 can be of any shape, a circle or a set of points and/or a set of lines as non limitative examples could be used. It is however advantageous to use a predetermined shaped pattern projection 26 using a major part of the dimensions of the image or improving accuracy of the results.

It is also worth mentioning that in the preferred embodiment of the system of the present invention, the camera 18 is advantageously provided with zooming means for zooming on the surface under inspection if more accurate measures are required. Indeed, in a zooming position, the camera 18 will provide images of smaller portions of the surface under inspection, these images having a better precision since the size of each pixel in real dimension, i.e. the pixelsize, will be smaller. For example, in a preferred embodiment using a pattern projection 26 having first and second line projections 28, 30 parallel to each other, let say that the line projections 28, 30 are spaced apart of 500 pixels in the image. In this case, the precision of the measures will be of 0.02 mm/pixel. If a zoom is performed on the surface under inspection, the line projection 28, 30 will be spaced apart of more than 500 pixels and the precision of the measures will then be better than 0.02 mm/pixel.

In a preferred embodiment, the inspection system 10 is manually operated by an operator. In this case, the system is advantageously further provided with a remote station (not shown) having a display 36 operatively coupled to the imaging means for receiving and displaying the images of the selected portion to the operator of the system, as illustrated in FIG. 2. The remote station preferably has control means for allowing the operator to rotate the imaging means in any direction in order to image any selected portion of the internal surface 20. Of course, as previously mentioned, the control means may also advantageously provide to the operator the possibility of zooming on a particular portion. The inspection system 10 is also further advantageously provided with a processing unit (not shown) for processing at least one of the images to determine a measure of a physical characteristic of the selected portion, for example the width of a longitudinal crack 38, as the one illustrated in FIG. 3A.

As previously mentioned, according to the predetermined characteristics of the two-dimensional pattern projection 26 and the shape of this projection, i.e. its deformation if any, it is possible to determine the perpendicularity of the optical axis of the camera 18 with respect to the surface 20 under inspection.

From the above, it should be understood that, in a first method of operation, the method for inspecting the internal surface 20 of the pipeline 22 comprises the steps of:
a) providing an inspection system 10 adapted to travel in the pipeline 22, the inspection system being provided with imaging means for imaging a selected portion of the interior surface 20 of the pipeline 22;
b) projecting a two-dimensional pattern projection 26 on the selected portion of the internal surface 20 of the pipeline 22 in the field of view or the imaging means;
c) imaging the selected portion comprising the two-dimensional pattern projection 26; and
d) monitoring a shape of the two-dimensional pattern projection 26 for monitoring a perpendicularity of the optical axis of the imaging means with respect to the selected portion of the internal surface 20 of the pipeline 22 prior to inspection thereof.

Figure 4A:
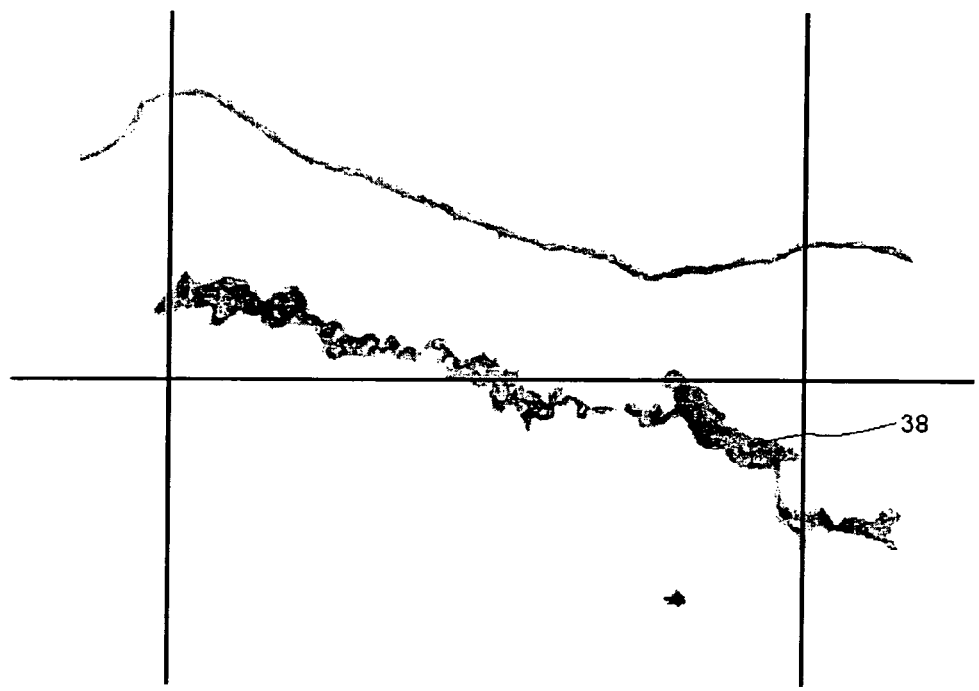
FIG. 4A shows another image of a longitudinal crack obtained with the system of the present invention.
Figure 4B:
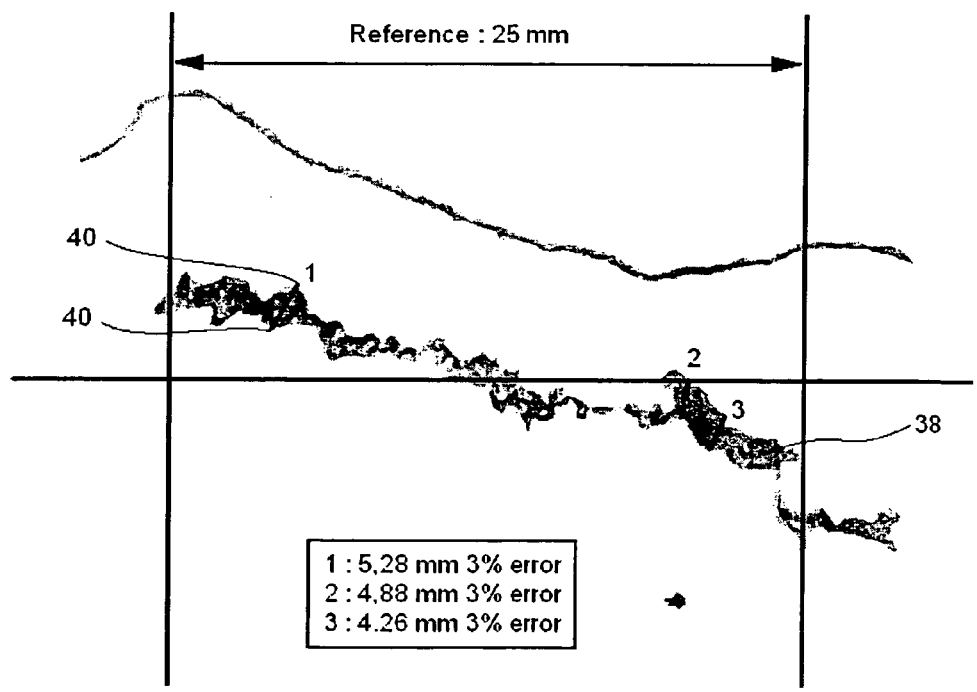
FIG. 4B shows the image of FIG. 4A wherein the inspection results have been displayed.

In the case wherein the inspection system 10 is manually operated by an operator, the operator preferably positions the camera 18 perpendicularly to the surface 20 under inspection with the help of the projected pattern. Once this step is done, the operator can manually measure defects appearing in the image, as illustrated in FIGS. 4A and 4B. For example, the operator can select points of interest on the projected reference lines 28, 30 to calibrate the inspection system 10, i.e. to determine the pixelsize. Then, he has to select points of interest 40 on each side of the crack 38. A software embedded in the processing unit can then perform the calculations in order to provide the operator with the measures of the selected points, according to the pixelsize previously determined. In FIG. 4B, the operator has selected points of interest 40 on each side of the crack 38 at three distinct positions and the processing unit calculates and displays the width of the crack 38 on the display.

It should be mentioned that in an alternate method of manual operation, the camera 18 has not to be positioned perpendicularly to the surface 20 under inspection. In this case, the processing unit is advantageously particularly adapted to calibrate the inspection system responsively to the shape of the two-dimensional pattern projection 26. In other words, the system determines the perpendicularity of the camera 18 with respect to the surface 20 under inspection and takes this information into consideration to provide corrected measures representing the actual size of the defect.

In another alternate embodiment, the method of operation can be further automatised. Indeed, the software can be designed to localise the defects without the help of an operator. The system can also be designed to take measures without having to position the camera 18 perpendicularly to the surface 20, as explained above. However, for a particular application, it is envisaged to provide control means for controlling a rotation of the camera 18 responsively to the shape of the two-dimensional pattern projection 26. In this case, the camera 18 will advantageously be rotated for extending perpendicularly to the surface 20 under inspection.

It should be understood that the system can be fully automated to perform the calibration of the system, i.e. the determination of the pixelsize, the detection of the defects and the measures thereof. In fact, an embedded software can be used to first automatically detect the two dimensional pattern projection and determine the pixelsize, as explained above. Then the software can analyse the images to detect potential defects and provide accurate measurements thereof. Of course, the software could be used for calibration purpose only while the inspection remains manually performed by the operator.

In a further embodiment, the frame is advantageously provided with an encoder or any convenient means allowing to determine the relative position of the inspection system inside the pipe. This is particularly advantageous for the measure of longitudinal cracks. As previously mentioned, the imaging means could also be adapted to zoom on the surface under inspection if more accurate measures are required.

As previously mentioned, the present inspection system is particularly advantageous over those of the prior art in that it is capable of providing very accurate results with a precision of the order of a hundredth of millimeter. Moreover, it can be understood upon reading of the present description that the system and method can be easily implement and is easy to use.

Although preferred embodiments of the present invention have beer described in detail herein and illustrated in the accompanying drawings, it is to be understood that the invention is not limited to these precise embodiments and that various changes and modifications may be effected therein without departing from the scope of the present invention.

What is claimed is:

1. An inspection system for inspecting an interior surface of a pipeline, said system comprising:
a frame adapted to travel in the pipeline;
a camera for imaging a selected portion of the interior surface of the pipeline, said camera having an optical axis and a field of view and being mounted in a rotatable manner on the frame; and
a two-dimensional pattern generator for generating a two-dimensional pattern projection, said generator being mounted with the camera to project the two-dimensional pattern projection in the field of view of the camera, the two-dimensional pattern projection comprising at least two line projections parallel to each other;
wherein the camera provides images of the selected portion of the internal surface comprising the two-dimensional pattern projection for monitoring a perpendicularity of the optical axis of the camera with respect to the selected portion of the interior surface of the pipeline thanks to a deformation of a shape of the two-dimensional pattern projection, wherein said generator is mounted proximate the optical axis of the camera to project the two-dimensional pattern projection in parallel with the optical axis of the camera; and
a remote station operatively coupled to the camera for receiving and displaying said images of the selected portion to an operator, the remote station comprising a processing unit configured for receiving an identification of at least two points of interest on said images from the operator, the at least two points of interest defining a physical characteristic of the selected portion, the processing unit being further configured for determining a distance in pixels between the at least two points of interest and determining a dimension of the physical characteristic from the distance in pixels, and wherein said processing unit is further adapted to calibrate the inspection system responsively to the shape of the two-dimensional pattern projection.

2. The inspection system according to claim 1, further comprising a light source for lighting the selected portion of the interior surface of the pipeline.

3. The inspection system according to claim 1, wherein said two-dimensional pattern projection is H-shaped.

4. The inspection system according to claim 1, wherein said two-dimensional pattern projection comprises a first and a second line projection parallel to each other and a third line projection perpendicular to the first and second.

5. The inspection system according to claim 1, wherein said two-dimensional pattern projection comprises a circle projection.

6. The inspection system according to claim 1, wherein said two-dimensional pattern projection comprises a set of points and a set of lines.

7. The inspection system according to claim 1, wherein said two-dimensional pattern generator comprises a first and a second laser generator for respectively generating a first and a second laser cross.

8. The inspection system according to claim 1, wherein the remote station is adapted to control rotation of the camera with respect to the frame.

9. The inspection system according to claim 1, wherein the remote station is adapted to control rotation of the camera with respect to the frame responsively to the shape of the two-dimensional pattern projection.

10. A method for inspecting an interior surface of a pipeline, said method comprising steps of:
a) providing an inspection system adapted to travel in the pipeline, said inspection system being provided with a camera for imaging a selected portion of the interior surface of the pipeline;
b) projecting a two-dimensional pattern projection on the selected portion of the interior surface of the pipeline in the field of view of the camera and in parallel with the optical axis of the camera, the two-dimensional pattern projection comprising a first and a second laser line projection parallel to each other;
c) calibrating the inspection system according to the shape of the two-dimensional pattern projection;
d) imaging the selected portion comprising the two-dimensional pattern projection; and
e) monitoring a deformation of a shape of the two-dimensional pattern projection for monitoring a perpendicularity of the optical axis of the camera with respect to the selected portion of the interior surface of the pipeline;
f) displaying images of the selected portion to an operator;
g) receiving an identification of at least two points of interest on said images from the operator, the at least two points of interest defining a physical characteristic of the selected portion;
h) determining a distance in pixels between the at least two points of interest;
i) determining a dimension of the physical characteristic from the distance in pixels.

11. The method according to claim 10, further comprising a step of rotating the camera according to the shape of the two-dimensional pattern projection until the optical axis of the camera extends perpendicularly to the selected portion of the internal surface of the pipeline prior to inspection thereof.

12. The method according to claim 10, wherein said step of measuring comprises a step of measuring a width of a crack.

13. The method according to claim 10, wherein the step of projecting comprises a step of projecting a third laser line projection perpendicularly to the first and second.

* * * * *

UNITED STATES PATENT AND TRADEMARK OFFICE
CERTIFICATE OF CORRECTION

| | | |
|---|---|---|
| PATENT NO. | : 8,345,094 B2 | Page 1 of 1 |
| APPLICATION NO. | : 12/515633 | |
| DATED | : January 1, 2013 | |
| INVENTOR(S) | : Daniel Demers | |

It is certified that error appears in the above-identified patent and that said Letters Patent is hereby corrected as shown below:

Title page, item [73] assignee: should read as follows:
-- 9022-5582 Quebec Inc. (C-Tec) --

Signed and Sealed this
Fourteenth Day of May, 2013

Teresa Stanek Rea
*Acting Director of the United States Patent and Trademark Office*